United States Patent
Park et al.

(10) Patent No.: US 9,030,664 B2
(45) Date of Patent: May 12, 2015

(54) APPARATUS FOR MEASURING TRANSMISSIVITY OF PATTERNED GLASS SUBSTRATE

(75) Inventors: Kyungwook Park, ChungCheongNam-Do (KR); YoonYoung Kwon, ChungCheongNam-Do (KR); Jaeyoung Choi, ChungCheongNam-Do (KR); Jongsung Lee, ChungCheongNam-Do (KR); Hoikwan Lee, ChungCheongNam-Do (KR); Seo-Yeong Cho, ChungCheongNam-Do (KR); Kyungmin Yoon, ChungCheongNam-Do (KR)

(73) Assignee: Samsung Corning Precision Materials Co., Ltd. (KR)

( * ) Notice: Subject to any disclaimer, the term of this patent is extended or adjusted under 35 U.S.C. 154(b) by 35 days.

(21) Appl. No.: 13/334,845

(22) Filed: Dec. 22, 2011

(65) Prior Publication Data
US 2012/0170040 A1  Jul. 5, 2012

(30) Foreign Application Priority Data

Dec. 30, 2010 (KR) .................. 10-2010-0139257

(51) Int. Cl.
*G01N 21/00* (2006.01)
*G01N 21/958* (2006.01)
*G01N 21/59* (2006.01)

(52) U.S. Cl.
CPC .............. *G01N 21/958* (2013.01); *G01N 21/59* (2013.01)

(58) Field of Classification Search
CPC .......... G01J 1/04; G01J 1/0407; G01J 1/0411; G01J 1/0422
See application file for complete search history.

(56) References Cited

U.S. PATENT DOCUMENTS

| | | | | |
|---|---|---|---|---|
| 4,719,152 A | * | 1/1988 | Ohta et al. | 428/432 |
| 5,712,709 A | * | 1/1998 | Task et al. | 356/432 |
| 5,731,898 A | * | 3/1998 | Orzi et al. | 359/587 |
| 5,776,219 A | * | 7/1998 | Jinbo et al. | 65/31 |
| 5,889,593 A | * | 3/1999 | Bareket | 356/445 |

(Continued)

FOREIGN PATENT DOCUMENTS

| | | |
|---|---|---|
| CN | 1519558 | 8/2004 |
| CN | 2751301 Y | 1/2006 |

(Continued)

OTHER PUBLICATIONS

Hsueh-Ling Yu, Comparison of different measurement methods for transmittance haze, Industrial Technology Research Inst., Jun. 2, 2009.

(Continued)

*Primary Examiner* — Gordon J Stock, Jr.
(74) *Attorney, Agent, or Firm* — Lerner, David, Littenberg, Krumholz & Mentlik, LLP

(57) ABSTRACT

An apparatus for measuring transmissivity of a patterned glass substrate. A beam radiator radiates a laser beam. A collimation lens collimates the laser beam radiated from the laser beam radiator. A beam expander expands a size of the laser beam collimated by the collimation lens. A detector has a light-receiving section, which receives the laser beam that has passed through the patterned glass substrate after having been expanded by the beam expander. A measuring instrument measures a transmissivity of the patterned glass substrate using the laser beam received by the detector.

4 Claims, 4 Drawing Sheets

(56) References Cited

U.S. PATENT DOCUMENTS

| | | | |
|---|---|---|---|
| 5,953,120 A * | 9/1999 | Hencken et al. | 356/339 |
| 6,025,919 A * | 2/2000 | Hidalgo et al. | 356/432 |
| 6,295,151 B1 * | 9/2001 | Nagai | 398/195 |
| 6,816,246 B2 * | 11/2004 | Akiyama et al. | 356/124 |
| 7,123,356 B1 * | 10/2006 | Stokowski et al. | 356/237.2 |
| 7,846,641 B2 * | 12/2010 | Satoh et al. | 430/311 |
| 2005/0039788 A1 | 2/2005 | Blieske et al. | |
| 2006/0209304 A1 | 9/2006 | Simpson et al. | |
| 2010/0237895 A1 * | 9/2010 | Chung | 324/766 |
| 2011/0013284 A1 * | 1/2011 | Ushigome | 359/576 |
| 2011/0029286 A1 * | 2/2011 | Kim et al. | 702/189 |
| 2011/0101226 A1 * | 5/2011 | Ben-Zvi et al. | 250/358.1 |
| 2011/0157551 A1 | 6/2011 | Plamann et al. | |
| 2011/0265840 A1 * | 11/2011 | Sela | 136/244 |

FOREIGN PATENT DOCUMENTS

| | | |
|---|---|---|
| CN | 101915751 A | 12/2010 |
| FR | 2832811 A1 | 5/2003 |
| GB | 2206429 | 1/1989 |
| JP | 52-067384 | 6/1977 |
| JP | 06288899 A * | 10/1994 |
| JP | 08261926 | 10/1996 |
| JP | 11204606 | 7/1999 |
| JP | 2003247913 | 9/2003 |
| JP | 2003307465 A * | 10/2003 |
| JP | 2005510751 A | 4/2005 |
| JP | 2005183655 A | 7/2005 |
| JP | 2006098389 A | 4/2006 |
| JP | 2007112697 A * | 5/2007 |
| JP | 2007278918 A * | 10/2007 |
| JP | 2007315990 | 12/2007 |
| JP | 2009281930 A | 12/2009 |
| JP | 2012028621 A * | 2/2012 |
| JP | 2012047732 A * | 3/2012 |
| WO | 2007097454 A1 | 8/2007 |
| WO | 2010026358 | 3/2010 |

OTHER PUBLICATIONS

Chinese Office Action for Application No. 201110456125.1 dated Dec. 27, 2013.

Korean Office Action for Application No. 10-2010-0139257 dated Dec. 24, 2013.

* cited by examiner

US 9,030,664 B2

APPARATUS FOR MEASURING TRANSMISSIVITY OF PATTERNED GLASS SUBSTRATE

CROSS REFERENCE TO RELATED APPLICATION

The present application claims priority from Korean Patent Application Number 10-2010-0139257 filed on Dec. 30, 2010, the entire contents of which application are incorporated herein for all purposes by this reference.

BACKGROUND OF THE PRESENT INVENTION

1. Field of the Present Invention

The present invention relates to an apparatus for measuring transmissivity, and more particularly, to a relatively simple apparatus for measuring transmissivity, which can measure the transmissivity of a patterned glass substrate.

2. Description of Related Art

Recently, in response to shortages of energy and resources and environmental pollution, the development of high-efficiency photovoltaic modules is underway on a large scale. For photovoltaic modules, the transmissivity of a cover substrate, e.g., a glass substrate, has an effect on the efficiency of photovoltaic modules. Accordingly, massive research and development is underway in order to increase transmissivity, for example, by minimizing internal absorption using a glass substrate composition or by improving transmissivity using a coating. In addition, two-dimensional (2D) array patterning is also performed to form a pattern in the surface of a glass substrate on which light is incident in order to increase the transmissivity of the glass substrate.

At present, patterned glass substrates are widely used not only for photovoltaic modules, but also for flat panel displays (PDPs). Glass substrate manufacturers precisely examine, in real time, the transmissivity of patterned glass substrates, which are continuously produced, by radiating light onto the patterned glass substrates in the process of manufacturing the patterned glass substrates.

As a device for measuring the transmissivity of patterned glass substrates, a spectrometer is used in the related art. However, ISO 9050 International Standard regulates that the transmissivity of a glass substrate by solar light be calculated by multiplying wavelength-dependent transmissivity with the wavelength-dependent sensitivity weight factor of a measuring standard light source D65 and a measuring device. Accordingly, the spectrometer of the related art is configured such that it exhibits wavelength-dependent transmissivity by receiving all visible wavelengths of light ranging from 380 nm to 780 nm and then processing them. That is, in order to measure the transmissivity of a glass substrate using the spectrometer of the related art, all of the wavelength-dependent transmissivities of the glass substrate of interest must be measured.

FIG. 1 is an example view depicting the process by which incident light is received by a spectrometer, in which the transmissivity of a patterned glass substrate of the related art is measured, and FIG. 2 is view depicting laser beam profiles on a patterned glass substrate and a glass substrate without a pattern after the laser beam has passed through the glass substrates. Here, reference numeral "20" is an integrating sphere, and "21" is a detector that receives light. FIG. 2 (a) shows the laser beam profile, which is diffused after the laser beam has passed through the patterned glass substrate, and FIG. 2 (b) shows the laser beam profile, which is diffused after the laser beam has passed through the glass substrate without a pattern.

As shown in FIG. 1, the spectrometer of the related art fails to precisely measure the transmissivity of the patterned glass substrate because the incident light is greatly diffused after having passed through the patterned glass substrate. This is because the detector 21 of the integrating sphere 20 may fail to receive light if the incident light is greatly diffused after having passed through the patterned glass substrate, as can be seen from FIG. 2 (a). Accordingly, there is a problem in that, when the transmissivity of the patterned glass substrate is measured using the spectrometer of the related art, the result is unreliable. There is another problem in that the transmissivity of the patterned glass substrate is underestimated.

The information disclosed in this Background of the present invention section is only for the enhancement of understanding of the background of the present invention, and should not be taken as an acknowledgment or any form of suggestion that this information forms a prior art that would already be known to a person skilled in the art.

BRIEF SUMMARY OF THE PRESENT INVENTION

Various aspects of the present invention provide an apparatus for measuring transmissivity, which can measure the transmissivity of a patterned glass substrate with high reliability.

Also provided is an apparatus for measuring transmissivity, which can prevent the transmissivity of the patterned glass substrate, which greatly diffuses light that is passing through it, from being underestimated.

In an aspect of the present invention, the apparatus for measuring transmissivity of a patterned glass substrate includes a beam radiator, which radiates a laser beam; a collimation lens, which collimates the laser beam; a beam expander, which expands the size of the laser beam collimated by the collimation lens; a detector having a light-receiving section, which receives the laser beam that has passed through the patterned glass substrate after having been expanded by the beam expander; and a measuring instrument, which measures the transmissivity of the patterned glass substrate using the laser beam received by the detector.

In an exemplary embodiment of the present invention, the beam expander expands the laser beam that is incident on the patterned glass substrate after having been expanded by the beam expander has a size such that it is incident on at least 10 pattern units of the patterned glass substrate.

According to embodiments of the present invention the apparatus for measuring the transmissivity of a patterned glass substrate is implemented so as to include the laser beam radiator, the mirror, the collimation lens, the beam expander, the detector and the measuring instrument, in which a laser beam that is incident on the patterned glass substrate after having een expanded by the beam expander has a size such that it is incident on at least 10 pattern units of the patterned glass substrate. Accordingly, the apparatus can advantageously measure the transmissivity of the patterned glass substrate with high reliability even though incident light is greatly diffused by the patterned glass substrate.

In addition, according to embodiments of the present invention, the apparatus for measuring transmissivity of a patterned glass is implemented such that it measures the representative transmissivity using a single wavelength, the wavelength weight factor of which is the maximum, without having to use a complicated wavelength-dividing optical device. As advantageous effects, the apparatus can be relatively simply fabricated, thereby reducing its manufacturing cost.

Furthermore, according to embodiments of the present invention, the apparatus for measuring the transmissivity of a patterned glass can be advantageously miniaturized such that it is applicable to the process of verifying the transmissivity in the actual process of manufacturing glass substrates.

In addition, according to embodiments of the present invention, the apparatus for measuring the transmissivity of a patterned glass can be used for an apparatus for measuring the transmissivity of cover glasses of photovoltaic cells.

The methods and apparatuses of the present invention have other features and advantages which will be apparent from, or are set forth in greater detail in the accompanying drawings, which are incorporated herein, and in the following Detailed Description of the present invention, which together serve to explain certain principles of the present invention.

DETAILED DESCRIPTION OF THE PRESENT INVENTION

Reference will now be made in detail to various embodiments of the present invention, examples of which are illustrated in the accompanying drawings and described below, so that a person having ordinary skill in the art to which the present invention relates can easily put the present invention into practice. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

Figure 3:
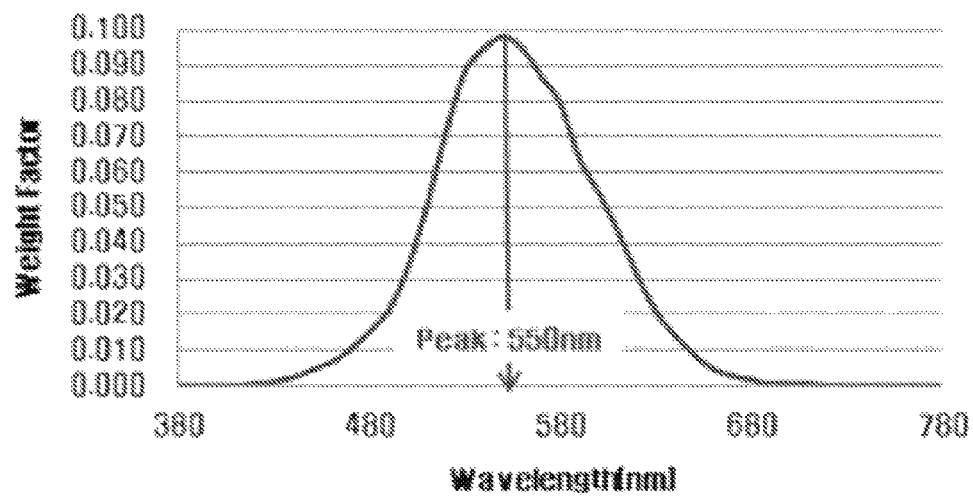
FIG. 3 is a graph depicting weight factors depending on wavelengths, which are presented in the ISO 9050 International Standard.

FIG. 3 is a graph depicting weight factors depending on wavelengths, which are set forth in the ISO 9050 International Standard.

The ISO 9050 International Standard regulates that the transmissivity of a glass substrate to solar light be calculated by multiplying the wavelength-dependent transmissivity by a wavelength-dependent sensitivity weight factor of a measuring standard light source D65 and a measuring device. Then, a spectrometer of the related art is realized such that it yields wavelength-dependent transmissivities by receiving all visible wavelengths of light ranging from 380 nm to 780 nm and then processing them. However, if the transmissivities are calculated according to the method set forth in the ISO 9050 International Standard, the transmissivities at wavelengths having a low weight factor are close to 0, and thus are not substantially added to the overall transmissivity.

Table 1 below presents data obtained by measuring the transmissivity of a flat glass substrate without a pattern according to the regulation of the ISO 9050 International Standard and data obtained by measuring a maximum weight factor wavelength, e.g. transmissivity at 550 nm.

TABLE 1

| Classification | Transmissivity (%) |
|---|---|
| IS 9050 International Standard | 91.39 |
| Maximum weight factor wavelength (550 nm) | 91.34 |
| Deviation | 0.05 |

As is apparent from Table 1 above, it can be appreciated that, when the ISO 9050 transmissivity calculated by receiving all visible wavelengths of light ranging from 380 nm to 780 nm is compared with the transmissivity calculated merely by receiving the maximum weight factor wavelength, the difference between the two values is about 0.05%, which is a very small value.

Accordingly, the apparatus for measuring the transmissivity of a patterned glass substrate according to an exemplary embodiment of the present invention is implemented as a relatively simple apparatus, which measures the transmissivity of the glass substrate at a wavelength at which the weight factor per wavelength is the maximum, e.g., 550 nm.

Figure 4:
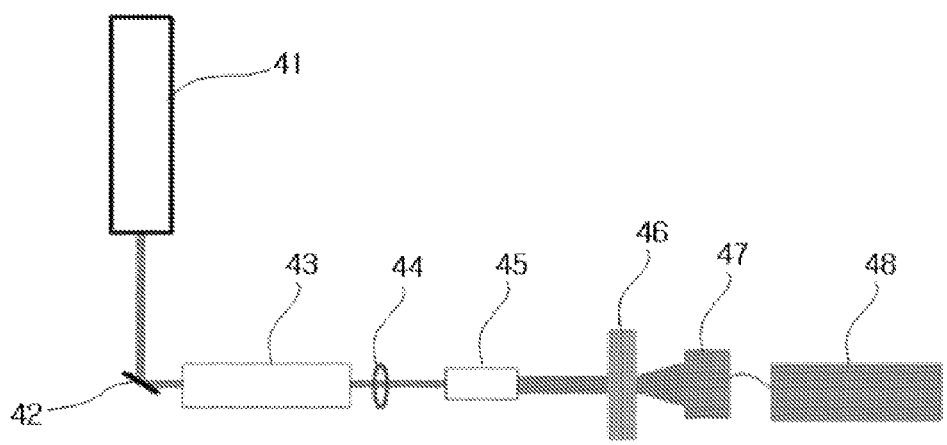
FIG. 4 is a view showing the configuration of an apparatus for measuring the transmissivity of a patterned glass substrate according to an exemplary embodiment of the present invention.

FIG. 4 is a view showing the configuration of an apparatus for measuring the transmissivity of a patterned glass substrate according to an exemplary embodiment of the present invention.

As shown in FIG. 4, the apparatus for measuring the transmissivity of a patterned glass substrate of this embodiment includes a laser beam radiator 41, a mirror 42, a collimation lens 44, a beam expander 45, a detector 47, and a measuring section 48.

The laser beam radiator 41 radiates a laser beam. In an example, the laser beam radiator 41 may be implemented so as to include a laser oscillator, which generates the laser beam, a radiating section, which guides the laser beam to the mirror 42, and a controller, which controls the laser oscillator. As examples thereof, the laser beam radiator may be implemented as one selected from among a YAG laser, a YLF laser and a YVO4 laser. It is preferred that the wavelength of the laser beam that is radiated from the laser beam radiator 41 be a wavelength at which the weight factor per wavelength is the maximum, e.g., a single wavelength of 550 nm.

The mirror 42 reflects the laser beam that is radiated from the laser beam radiator 41. The collimation lens 44 collimates the laser beam that is reflected from the mirror 42.

The beam expander 45 is a device that expands the size of the laser beam that is collimated by the collimation lens 44. The beam expander 45 allows a worker to measure the transmissivity of a patterned glass substrate 46, which may have a variety of sizes and shapes of patterns.

Figure 1:
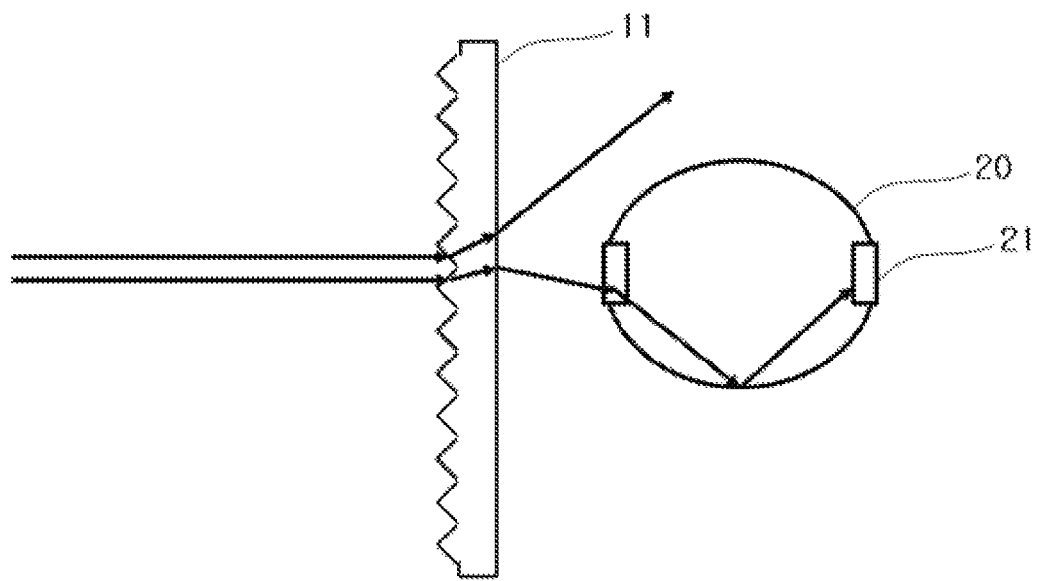
FIG. 1 is an example view depicting the process in which incident light is received by a spectrometer, which measures the transmissivity of a patterned glass substrate of the related art.
Figure 2:
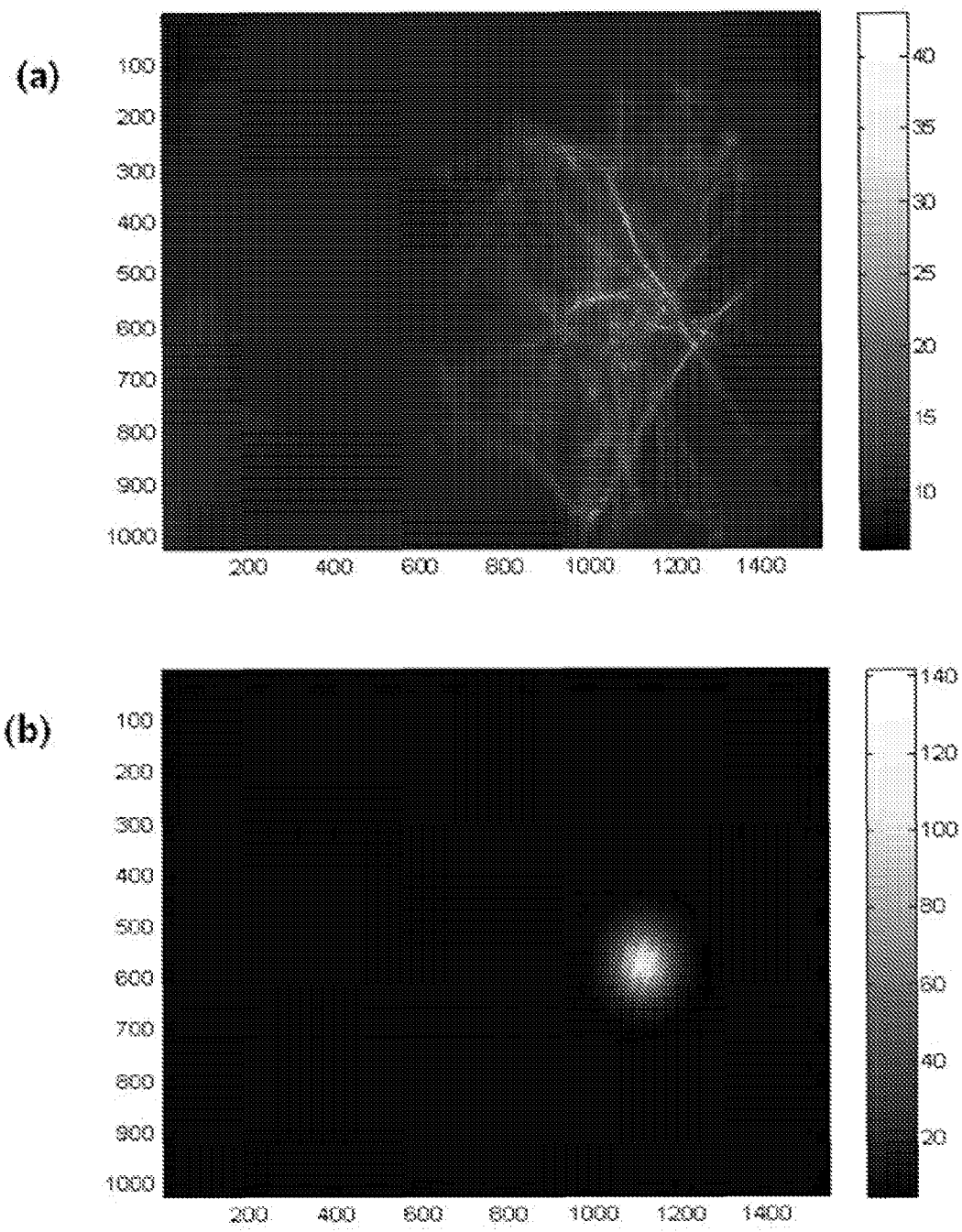
FIG. 2 is view depicting laser beam profiles on a patterned glass substrate and a glass substrate without a pattern after a laser beam has passed through the glass substrates.

It is preferred that the laser beam that is incident on the patterned glass substrate 46 after it is expanded by the beam expander have a size such that it is incident on at least 10 pattern units of the patterned glass substrate 46 (see triangular sections in FIG. 1), so that transmissivity can be precisely measured through the omission of variables from the measurement of transmissivity.

Here, the patterned glass substrate 46 is made of glass in most cases. Although a synthetic resin, such as acryl, polycarbonate, or fluorocarbon resin, is used in some cases, its use is limited to outdoor or domestic applications. The patterned glass substrate 46 is generally made of low-iron tempered glass having a low surface reflectivity in order to minimize self-reflection loss.

The detector 47 receives the laser beam that has passed through the patterned glass substrate 46 after having been expanded by the beam expander 45. The detector 47 includes a light-receiving section and a signal-processing section. It is preferred that the size of the light-receiving section of the detector 47 be at least two times as great as that of the laser beam that is incident on the patterned glass substrate 46 after having been expanded by the beam expander 45 in order to prevent reception loss.

It is preferred that the detector 47 be disposed such that it is as close as possible to the rear end of the patterned glass substrate 46 in order to prevent loss of the laser beam that has passed through the patterned glass substrate 46. In an example, the size of the detector 47 and the optimum position between the detector 47 and the glass substrate 46 can be optimized via simulation.

The measuring instrument 48 measures the transmissivity of the patterned glass substrate using the laser beam received by the detector 47.

In another embodiment, the apparatus for measuring the transmissivity of a patterned glass substrate of the present invention may be implemented so as to include a noise filter 43. The noise filter 43 removes noise from the laser beam that is reflected from the mirror 42. This can consequently reduce errors in the transmissivity measured by the measuring instrument 48, which would otherwise be caused by signal noises.

Figure 5:
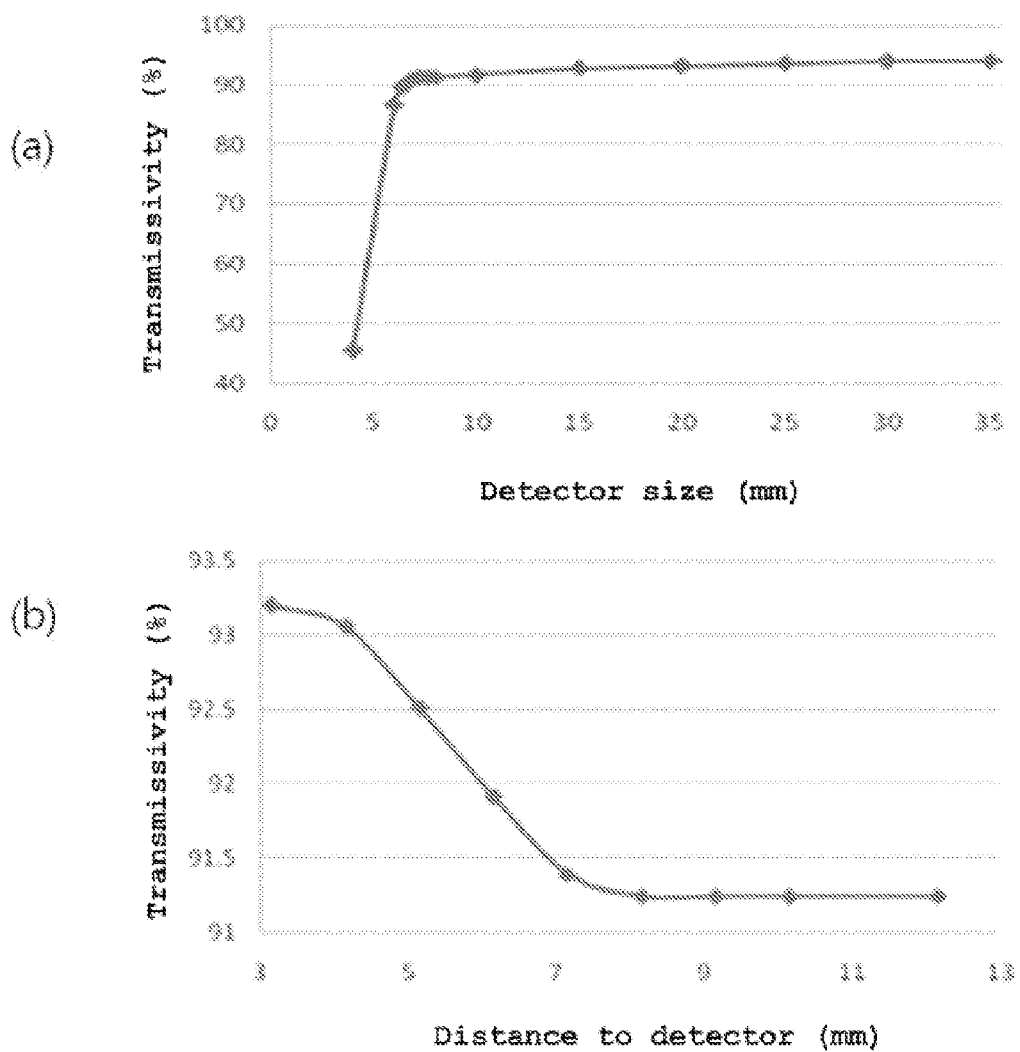
FIG. 5 is a graph depicting the characteristics of a detector, which is used in an apparatus for measuring the transmissivity of a patterned glass substrate according to an exemplary embodiment of the present invention.

FIG. 5 is a graph depicting the characteristics of a detector, which is used in an apparatus for measuring the transmissivity of a patterned glass substrate according to an exemplary embodiment of the present invention. Here, the beam expander is adjusted such that the length of one pattern unit of the patterned glass substrate is 0.5 mm and the laser beam that is incident on the patterned glass substrate after having been expanded by the beam expander is incident on at least 10 pattern units of the patterned glass substrate.

First, FIG. 5 (*a*) is a graph depicting the relationship between detector size and transmissivity. This shows that the transmissivity of the patterned glass substrate is 90% or more if the size of the light-receiving section of the detector is 10 mm or more. Accordingly, it can be appreciated that the size of the light-receiving section of the detector according an embodiment of the present invention is preferably at least two times the size, 5 mm, of the laser beam that is incident on the patterned glass substrate after having been expanded by the beam expander.

FIG. 5 (*b*) is a graph depicting the relationship between the distance from the detector to the patterned glass substrate and transmissivity. This shows that the transmissivity of the patterned glass substrate is 92.5% or more if the distance from the detector to the patterned glass substrate is 5 mm or less. As apparent from this, it is preferred that the detector according to an embodiment of the present invention be disposed such that it is as close as possible to the rear end of the patterned glass substrate in order to prevent loss of the laser beam that has passed through the patterned glass substrate.

The foregoing descriptions of specific exemplary embodiments of the present invention have been presented for the purposes of illustration and description. They are not intended to be exhaustive or to limit the present invention to the precise forms disclosed, and obviously many modifications and variations are possible in light of the above teachings. The exemplary embodiments were chosen and described in order to explain certain principles of the present invention and their practical application, to thereby enable others skilled in the art to make and utilize various exemplary embodiments of the present invention, as well as various alternatives and modifications thereof. It is intended that the scope of the present invention be defined by the Claims appended hereto and their equivalents.

What is claimed is:

1. A method for measuring transmissivity of a patterned glass substrate, comprising:
   radiating a laser beam having a size, at a single wavelength of 550 nm;
   collimating the laser beam with a collimation lens;
   expanding the size of the collimated laser beam;
   passing the expanded laser beam through a glass substrate having a plurality of pattern units on which the expanded collimated laser beam is incident;
   receiving, at a detector having a light-receiving section at least twice as large as a size of the expanded laser beam that is incident on the patterned glass substrate, the expanded laser beam that is passed through the patterned glass substrate; and
   measuring transmissivity of the patterned glass substrate based on the received laser beam;
   wherein the detector is 5 mm or less from a rear end of the patterned glass substrate.

2. The method of claim 1, wherein the collimated laser beam is expaned to such a size that the expanded laser beam can be incident on at least 10 pattern units of the patterned glass substrate.

3. The method of claim 1, further comprising reflecting the laser beam off of a mirror into the collimation lens.

4. The method of claim 3, further comprising using a noise filter to remove noise from the reflected laser beam.

* * * * *

UNITED STATES PATENT AND TRADEMARK OFFICE
CERTIFICATE OF CORRECTION

| | | |
|---|---|---|
| PATENT NO. | : 9,030,664 B2 | Page 1 of 1 |
| APPLICATION NO. | : 13/334845 | |
| DATED | : May 12, 2015 | |
| INVENTOR(S) | : Park et al. | |

It is certified that error appears in the above-identified patent and that said Letters Patent is hereby corrected as shown below:

In the Claims

Column 6, line 48, delete "expaned" and insert therefor -- expanded --.

Signed and Sealed this
First Day of March, 2016

Michelle K. Lee
*Director of the United States Patent and Trademark Office*